US009500619B2

(12) United States Patent
Ishikawa et al.

(10) Patent No.: US 9,500,619 B2
(45) Date of Patent: Nov. 22, 2016

(54) METHOD FOR PERFORMING PROCESSING ON GAS SENSOR

(71) Applicant: NGK INSULATORS, LTD., Nagoya-shi, Aichi (JP)

(72) Inventors: Tetsuya Ishikawa, Kasugai (JP); Kazuhito Sakakibara, Toyota (JP); Shota Kageyama, Aichi (JP)

(73) Assignee: NGK INSULATORS, LTD., Nagoya (JP)

( * ) Notice: Subject to any disclaimer, the term of this patent is extended or adjusted under 35 U.S.C. 154(b) by 80 days.

(21) Appl. No.: 14/642,088

(22) Filed: Mar. 9, 2015

(65) Prior Publication Data

US 2015/0260679 A1 Sep. 17, 2015

(30) Foreign Application Priority Data

Mar. 11, 2014 (JP) .................................. 2014-047029

(51) Int. Cl.
| | |
|---|---|
| *G01N 27/407* | (2006.01) |
| *G01N 27/41* | (2006.01) |
| *G01N 27/417* | (2006.01) |

(52) U.S. Cl.
CPC ............ *G01N 27/41* (2013.01); *G01N 27/407* (2013.01); *G01N 27/4076* (2013.01); *G01N 27/417* (2013.01)

(58) Field of Classification Search
CPC ................ G01N 27/41; G01N 27/407; G01N 27/4076; G01N 27/417
See application file for complete search history.

(56) References Cited

U.S. PATENT DOCUMENTS

| | | | |
|---|---|---|---|
| 5,902,469 A | 5/1999 | Kato et al. | |
| 6,290,840 B1 * | 9/2001 | Kato | .................... G01N 27/417 204/425 |

FOREIGN PATENT DOCUMENTS

| | | |
|---|---|---|
| JP | 3537983 B2 | 6/2004 |
| JP | 2006-284223 A | 10/2006 |

* cited by examiner

*Primary Examiner* — Arun S Phasge
(74) *Attorney, Agent, or Firm* — Global IP Counselors, LLP

(57) ABSTRACT

A sensor element mainly contains an oxygen ion conductive solid electrolyte. By applying, across a first electrode formed on a surface of an internal space into which a measurement gas is introduced from an outside and a second electrode formed on an external surface of the element, a predetermined voltage determined based on a potential difference between the first electrode and a reference electrode provided inside the element, oxygen in the internal space can be pumped out. In a case where pump reference processing is performed, a DC voltage having a maximum value of 1.4 to 2.0 V inclusive is applied across the reference and second electrodes for 10 to 1200 seconds inclusive in a state in which the reference and second electrodes are respectively electrically connected to negative and positive terminals of an external DC power supply, and an element temperature is set to 700 to 850° C. inclusive.

4 Claims, 5 Drawing Sheets

METHOD FOR PERFORMING PROCESSING ON GAS SENSOR

BACKGROUND OF THE INVENTION

1. Field of the Invention

The present invention relates to processing to suppress progress of oxidation of a reference electrode performed on a gas sensor and, in particular, on a sensor element for use in the gas sensor.

2. Description of the Background Art

Various gas sensors have been used to obtain the concentration of a desired gas component in a measurement gas. For example, as a device for measuring a NOx concentration in a measurement gas such as a combustion gas, a NOx sensor including a sensor element formed of an oxygen ion conductive solid electrolyte, such as zirconia ($ZrO_2$), is known (see, for example, Japanese Patent Application Laid-Open No. 2006-284223 and Japanese Patent No. 3537983).

A sensor element of a gas sensor, including the NOx sensors disclosed in Japanese Patent Application Laid-Open No. 2006-284223 and Japanese Patent No. 3537983, obtains the concentration of a measurement-target gas component (target component) by making use of the fact that, when a measurement electrode decomposes the measurement-target gas component by its catalytic activity, the amount of oxygen ions generated at the time becomes proportional to current flowing between the measurement electrode and a reference electrode. Specifically, the relationship (sensitivity characteristics or concentration profiles) between a concentration value and a current value (output signal value) in individual sensor elements is obtained in advance with use of a mixed gas containing a target component of a known concentration, and, when the sensor elements are actually used, a measured current value is converted into a concentration value based on the sensitivity characteristics to obtain the concentration value of the target component.

When a gas sensor as described above is used, processing called pump reference processing may be performed. In the pump reference processing, oxygen in an atmospheric gas existing around the gas sensor (e.g., an exhaust gas in a case where the gas sensor is mounted on an exhaust pipe of an automobile for use) is partially supplied from an outer pumping electrode to a reference electrode through use of an oxygen pumping function of an oxygen ion conductive solid electrolyte, so that an oxygen concentration in the vicinity of a surface of the reference electrode is kept constant.

The pump reference processing is generally processing of supplying oxygen to the vicinity of the surface of the reference electrode by connecting the reference electrode to a positive terminal of an external DC power supply, connecting the outer pumping electrode, which is originally used to pump oxygen out of the sensor element, to a negative terminal of the external DC power supply, and applying a DC voltage across the outer pumping electrode and the reference electrode. More specifically, when the voltage is applied across the electrodes by the external DC power supply, in the outer pumping electrode, oxygen is ionized upon reception of electrons and taken into the sensor element, whereas, in the reference electrode, oxygen ions are oxidized to oxygen upon release of electrons, and the oxygen remains in the vicinity of the surface of the reference electrode.

In a case where the gas sensor is continuously or intermittently used, however, problems such as an increase in electrical impedance (resistance) between the outer pumping electrode and the reference electrode over time as well as a large deviation, from an assumed value (control reference value), of electromotive force generated between the measurement electrode and the reference electrode or at another location during operation of the sensor element, and poor responsiveness of the sensor element have been confirmed. It is confirmed that these events are likely to occur when the pump reference processing is performed for a long time or frequently.

Simple omission of the pump reference processing itself, however, is not necessarily effective in terms of stabilization of the oxygen concentration in the vicinity of the reference electrode. The reference electrode is used as a reference when the concentration of the measurement-target gas component is obtained (more specifically, a reference when oxygen pumping current required to calculate the concentration is obtained), and, in this regard, performing the pump reference processing is sufficiently meaningful.

SUMMARY OF THE INVENTION

The present invention relates to a method for performing processing on a gas sensor, and is, in particular, directed to processing to suppress progress of oxidation of a reference electrode performed on a sensor element for use in the gas sensor.

The present invention is a method for performing processing on a gas sensor having a sensor element containing an oxygen ion conductive solid electrolyte as a major component. The sensor element includes: an internal space into which a measurement gas is introduced from an external space; a first electrode formed on a surface of the internal space; a second electrode formed on an external surface of the sensor element; and a reference electrode provided inside the sensor element. The sensor element is configured to be capable of pumping out oxygen in the internal space by applying, across the first electrode and the second electrode, a predetermined voltage determined based on a potential difference between the first electrode and the reference electrode. The sensor element is configured to be capable of stabilizing an oxygen concentration in the vicinity of a surface of the reference electrode by electrically connecting the reference electrode to a positive terminal of a first external DC power supply, electrically connecting the second electrode to a negative terminal of the first external DC power supply, and continuously or intermittently applying a DC voltage across the reference electrode and the second electrode. In this case, the method includes the steps of: a) electrically connecting the reference electrode to a negative terminal of a second external DC power supply, and electrically connecting the second electrode to a positive terminal of the second external DC power supply; and, b) in an electrically-connected state created by the step a), applying a DC voltage having a maximum value of 1.4 V to 2.0 V inclusive across the reference electrode and the second electrode for 10 seconds to 1200 seconds inclusive while setting temperature of the sensor element to 700° C. to 850° C. inclusive.

According to the present invention, the progress of oxidation of the reference electrode can be suppressed. The condition of the reference electrode is thereby stabilized, and thus reduction in measurement accuracy of the gas sensor can be suppressed.

The object of the present invention is therefore to provide a method for performing processing on a gas sensor that can stabilize the condition of the reference electrode and suppress the reduction in measurement accuracy of the gas sensor.

DESCRIPTION OF THE PREFERRED EMBODIMENTS

Outline Configuration of Gas Sensor

An outline configuration of a gas sensor 100 to which a method for performing processing according to the present embodiment is applied is described first.

Figure 1:
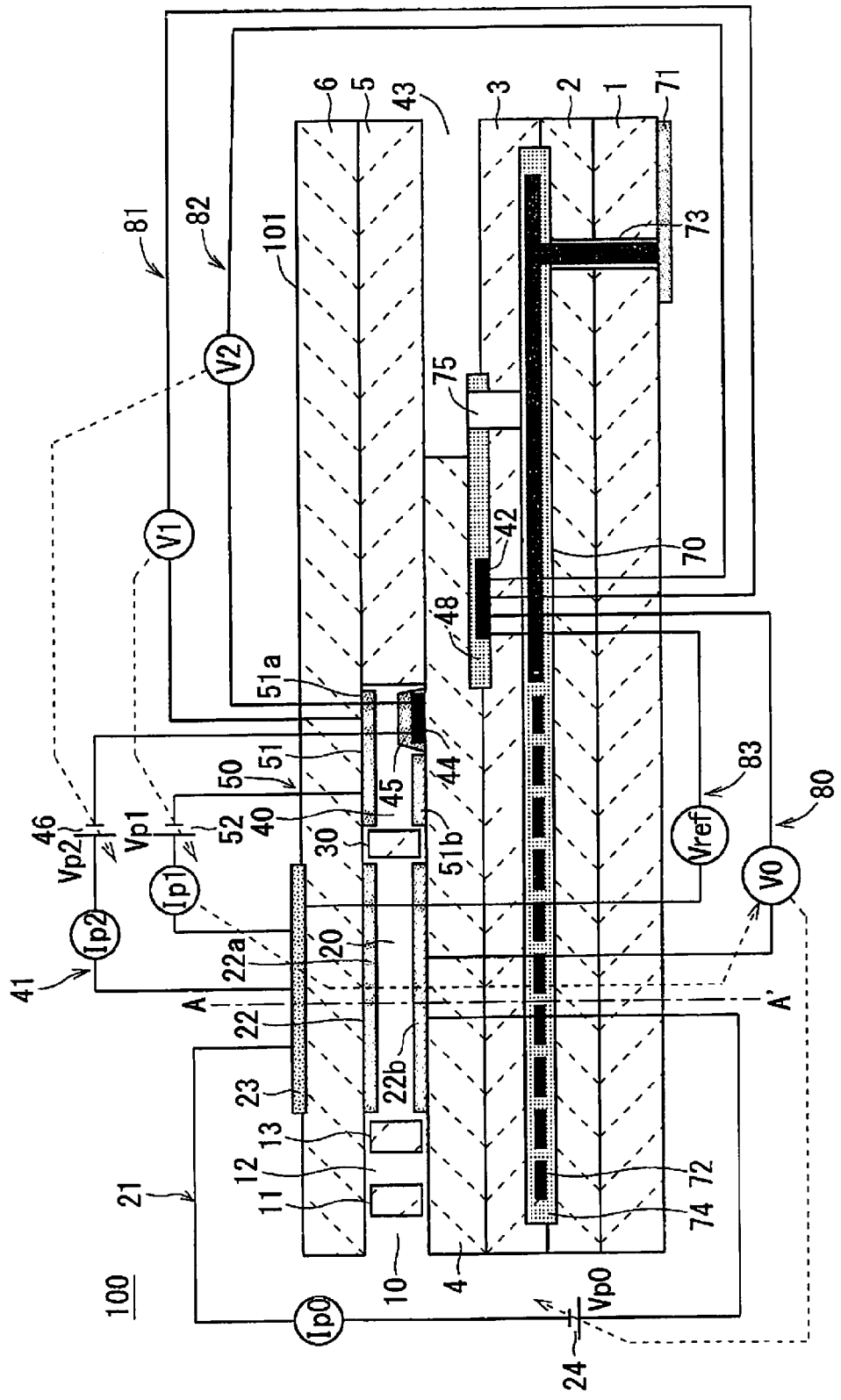
FIG. 1 is a schematic cross section schematically showing an example of configuration of a gas sensor 100.

FIG. 1 is a schematic cross section schematically showing an example of the configuration of the gas sensor 100. A sensor element 101 is an element having a structure in which six layers, namely, a first substrate layer 1, a second substrate layer 2, a third substrate layer 3, a first solid electrolyte layer 4, a spacer layer 5, and a second solid electrolyte layer 6, which are each an oxygen ion conductive solid electrolyte layer formed, for example, of zirconia ($ZrO_2$), are laminated in the stated order from a bottom side of FIG. 1. Solid electrolytes that form these six layers are dense and airtight. The sensor element 101 is manufactured, for example, by performing predetermined machining and printing of circuit patterns with respect to ceramic green sheets corresponding to respective layers, then laminating these green sheets, and further baking the laminated green sheets for integration.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are formed adjacent to each other so as to communicate in the stated order.

The gas inlet 10, the buffer space 12, the first internal space 20, and the second internal space 40 are spaces inside the sensor element 101 that look as if they were provided by hollowing out the spacer layer 5, and that have an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (openings whose longitudinal direction is a direction perpendicular to the plane of FIG. 1). A part extending from the gas inlet 10 to the second internal space 40 is also referred to as a gas distribution part.

At a location farther from the end portion than the gas distribution part is, a reference gas introduction space 43 having a side portion defined by a side surface of the first solid electrolyte layer 4 is provided between an upper surface of the third substrate layer 3 and a lower surface of the spacer layer 5. As a reference gas used when a NOx concentration is measured, the atmosphere is introduced into the reference gas introduction space 43, for example.

An atmosphere introduction layer 48 is a layer formed of porous alumina, and the reference gas is introduced into the atmosphere introduction layer 48 through the reference gas introduction space 43. The atmosphere introduction layer 48 is formed so as to cover a reference electrode 42.

The reference electrode 42 is a porous cermet electrode formed so as to be sandwiched between the upper surface of the third substrate layer 3 and the first solid electrolyte layer 4, and the atmosphere introduction layer 48 leading to the reference gas introduction space 43 is provided around the reference electrode 42, as described above. As described later, an oxygen concentration (oxygen partial pressure) in the first internal space 20 and the second internal space 40 can be measured with use of the reference electrode 42.

Since the atmosphere is introduced into the reference gas introduction space 43, the oxygen concentration inside the reference gas introduction space 43 is substantially equal to the oxygen concentration in the atmosphere. The oxygen concentration, however, can vary depending on water•vapor and other substances entering into the atmosphere, and thus the oxygen concentration in the vicinity of a surface of the reference electrode 42 can further be stabilized locally by performing pump reference processing, which is described later, in the gas sensor 100 according to the present embodiment.

In the gas distribution part, the gas inlet 10 opens to an external space, and a measurement gas is taken from the external space into the sensor element 101 through the gas inlet 10.

The first diffusion control part 11 applies predetermined diffusion resistance to the measurement gas taken through the gas inlet 10.

The buffer space 12 is provided to guide the measurement gas introduced from the first diffusion control part 11 to the second diffusion control part 13.

The second diffusion control part 13 applies predetermined diffusion resistance to the measurement gas introduced from the buffer space 12 into the first internal space 20.

When the measurement gas is introduced from the outside of the sensor element 101 into the first internal space 20, the measurement gas, which is abruptly taken into the sensor element 101 through the gas inlet 10 due to pressure fluctuation of the measurement gas in the external space (pulsation of exhaust pressure in a case where the measurement gas is an exhaust gas of an automobile), is not directly introduced into the first internal space 20, but introduced into the first internal space 20 after concentration fluctuation of the measurement gas is canceled through the first diffusion control part 11, the buffer space 12, and the second diffusion control part 13. As a result, the concentration fluctuation of the measurement gas introduced into the first internal space 20 is almost negligible.

The first internal space 20 is provided as a space used to adjust oxygen partial pressure in the measurement gas introduced through the second diffusion control part 13. The oxygen partial pressure is adjusted by an operation of a main pump cell 21.

The main pump cell 21 is an electrochemical pump cell constituted by an inner pump electrode 22, an outer pump electrode 23, and the second solid electrolyte layer 6 sandwiched between the inner pump electrode 22 and the outer pump electrode 23. The inner pump electrode 22 has a ceiling electrode portion 22a that is provided substantially on the entire lower surface of a part of the second solid electrolyte layer 6 facing the first internal space 20. The outer pump electrode 23 is provided in a region, on an upper surface of the second solid electrolyte layer 6, corresponding to the ceiling electrode portion 22a so as to be exposed to the external space.

The inner pump electrode 22 is formed over upper and lower solid electrolyte layers (the second solid electrolyte layer 6 and the first solid electrolyte layer 4) that define the first internal space 20, and the spacer layer 5 that provides a side wall to the first internal space 20. Specifically, the ceiling electrode portion 22a is formed on the lower surface of the second solid electrolyte layer 6, which provides a ceiling surface to the first internal space 20, a bottom electrode portion 22b is formed on the upper surface of the first solid electrolyte layer 4, which provides a bottom surface to the first internal space 20, and a side electrode portion (not illustrated) is formed on a side wall surface (internal surface) of the spacer layer 5 that forms both side wall portions of the first internal space 20 so as to connect the ceiling electrode portion 22a and the bottom electrode portion 22b. The inner pump electrode 22 is thereby provided in the form of a tunnel at a location where the side electrode portion is provided.

The inner pump electrode 22 and the outer pump electrode 23 are each formed as a porous cermet electrode (for example, a cermet electrode formed of $ZrO_2$ and Pt that contains Au of 1%). The inner pump electrode 22, which comes into contact with the measurement gas, is formed with use of a material having a weakened reducing ability with respect to a NOx component in the measurement gas.

The main pump cell 21 can pump out oxygen existing in the first internal space 20 to the external space or pump in oxygen existing in the external space to the first internal space 20 by applying a desired pump voltage Vp0 across the inner pump electrode 22 and the outer pump electrode 23 to allow pump current Ip0 to flow between the inner pump electrode 22 and the outer pump electrode 23 in a positive or negative direction.

In order to detect an oxygen concentration (oxygen partial pressure) in the atmosphere in the first internal space 20, the inner pump electrode 22, the second solid electrolyte layer 6, the spacer layer 5, the first solid electrolyte layer 4, the third substrate layer 3, and the reference electrode 42 constitute an electrochemical sensor cell, that is, a main-pump-control oxygen-partial-pressure detection sensor cell 80.

The oxygen concentration (oxygen partial pressure) in the first internal space 20 can be known by measuring electromotive force V0 in the main-pump-control oxygen-partial-pressure detection sensor cell 80.

Furthermore, the pump current Ip0 is controlled by performing feedback control of Vp0 so that the electromotive force V0 is kept constant. The oxygen concentration in the first internal space 20 can thereby be maintained at a predetermined constant value.

The third diffusion control part 30 applies predetermined diffusion resistance to the measurement gas having an oxygen concentration (oxygen partial pressure) controlled, in the first internal space 20, by the operation of the main pump cell 21, and guides the measurement gas to the second internal space 40.

The second internal space 40 is provided as a space used to perform processing concerning measurement of a nitrogen oxide (NOx) concentration in the measurement gas introduced through the third diffusion control part 30. The NOx concentration is measured, mainly in the second internal space 40 in which an oxygen concentration has been adjusted by an auxiliary pump cell 50, by an operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40. The oxygen concentration in the second internal space 40 can thereby be kept constant with high precision, and thus high-precision measurement of a NOx concentration can be achieved in the gas sensor 100.

The auxiliary pump cell 50 is an auxiliary electrochemical pump cell constituted by an auxiliary pump electrode 51, the outer pump electrode 23 (not limited to the outer pump electrode 23 but may be any appropriate electrode outside the sensor element 101), and the second solid electrolyte layer 6. The auxiliary pump electrode 51 has a ceiling electrode portion 51a that is provided substantially on the entire lower surface of a part of the second solid electrolyte layer 6 facing the second internal space 40.

The auxiliary pump electrode 51 is provided in the second internal space 40 in the form of a tunnel, as with the inner pump electrode 22 provided in the first internal space 20 described previously. That is to say, the ceiling electrode portion 51a is formed on the second solid electrolyte layer 6, which provides a ceiling surface to the second internal space 40, a bottom electrode portion 51b is formed on the first solid electrolyte layer 4, which provides a bottom surface to the second internal space 40, and a side electrode portion (not illustrated) that connects the ceiling electrode portion 51a and the bottom electrode portion 51b is formed on both wall surfaces of the spacer layer 5, which provides a side wall to the second internal space 40. The auxiliary pump electrode 51 is thereby provided in the form of a tunnel.

As with the inner pump electrode 22, the auxiliary pump electrode 51 is formed with use of a material having a weakened reducing ability with respect to a NOx component in the measurement gas.

The auxiliary pump cell 50 can pump out oxygen in the atmosphere existing in the second internal space 40 to the external space or pump in oxygen existing in the external space to the second internal space 40 by applying a desired voltage Vp1 across the auxiliary pump electrode 51 and the outer pump electrode 23.

In order to control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, that is, an auxiliary-pump-control oxygen-partial-pressure detection sensor cell 81.

The auxiliary pump cell 50 performs pumping through use of a variable power supply 52 whose voltage is controlled based on electromotive force V1 detected by the auxiliary-pump-control oxygen-partial-pressure detection sensor cell 81. The oxygen partial pressure in the atmosphere in the second internal space 40 is thereby controlled to a low partial pressure having substantially no effect on NOx measurement.

At the same time, resulting pump current Ip1 is used to control the electromotive force in the main-pump-control oxygen-partial-pressure detection sensor cell 80. Specifically, the pump current Ip1 is input, as a control signal, into the main-pump-control oxygen-partial-pressure detection sensor cell 80, and, by controlling the electromotive force V0 in the main-pump-control oxygen-partial-pressure detection sensor cell 80, the oxygen partial pressure in the measurement gas introduced through the third diffusion control part 30 into the second internal space 40 is controlled so as to have a gradient that is always constant. In use as a NOx sensor, the oxygen concentration in the second internal space 40 is maintained at a constant value of approximately 0.001 ppm by the action of the main pump cell 21 and the auxiliary pump cell 50.

The measurement pump cell 41 measures a NOx concentration in the measurement gas in the second internal space 40. The measurement pump cell 41 is an electrochemical pump cell constituted by a measurement electrode 44, the outer pump electrode 23, the second solid electrolyte layer 6, the spacer layer 5, and the first solid electrolyte layer 4. The measurement electrode 44 is provided on an upper surface of a part of the first solid electrolyte layer 4 facing the second internal space 40 so as to be separated from the third diffusion control part 30.

The measurement electrode 44 is a porous cermet electrode. The measurement electrode 44 also functions as a NOx reduction catalyst that reduces NOx existing in the atmosphere in the second internal space 40. The measurement electrode 44 is covered with a fourth diffusion control part 45.

The fourth diffusion control part 45 is a film formed of a porous body containing alumina ($Al_2O_3$) as a major component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of nitrogen oxides in the atmosphere around the measurement electrode 44, and detect the amount of generated oxygen as pump current Ip2.

In order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, that is, a measurement-pump-control oxygen-partial-pressure detection sensor cell 82. A variable power supply 46 is controlled based on electromotive force V2 detected by the measurement-pump-control oxygen-partial-pressure detection sensor cell 82.

The measurement gas introduced into the second internal space 40 reaches the measurement electrode 44 through the fourth diffusion control part 45 under a condition in which the oxygen partial pressure is controlled. Nitrogen oxides in the measurement gas around the measurement electrode 44 are reduced ($2NO \rightarrow N_2+O_2$) to generate oxygen. The generated oxygen is pumped by the measurement pump cell 41, and, at that time, a voltage Vp2 of the variable power supply 46 is controlled so that a control voltage V2 detected by the measurement-pump-control oxygen-partial-pressure detection sensor cell 82 is kept constant. The amount of oxygen generated around the measurement electrode 44 is proportional to a nitrogen oxide concentration in the measurement gas, and thus the nitrogen oxide concentration in the measurement gas is calculated with use of the pump current Ip2 in the measurement pump cell 41.

If the measurement electrode 44, the first solid electrolyte layer 4, the third substrate layer 3, and the reference electrode 42 are combined to constitute an oxygen partial pressure detection means as an electrochemical sensor cell, electromotive force according to a difference between the amount of oxygen generated through reduction of a NOx component in the atmosphere around the measurement electrode 44 and the amount of oxygen contained in a reference atmosphere can be detected, and a NOx component concentration in the measurement gas can thereby be obtained.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure in the measurement gas outside the sensor can be detected with use of electromotive force Vref obtained by the sensor cell 83.

In the gas sensor 100 having such a configuration, the measurement gas whose oxygen partial pressure is always maintained at a constant low value (a value having substantially no effect on NOx measurement) by operations of the main pump cell 21 and the auxiliary pump cell 50 is provided to the measurement pump cell 41. Therefore, a NOx concentration in the measurement gas can be known based on the pump current Ip2 allowed to flow, approximately in proportion to the NOx concentration in the measurement gas, by pumping out oxygen generated through reduction of NOx with the measurement pump cell 41.

The sensor element 101 further includes a heater part 70 playing a role in temperature adjustment of heating the sensor element 101 and keeping it warm to enhance oxygen ion conductivity of a solid electrolyte. The heater part 70 includes a heater electrode 71, a heater 72, a through hole 73, a heater insulating layer 74, and a pressure diffusion hole 75. The heater electrode 71 is an electrode formed so as to be in contact with a lower surface of the first substrate layer 1. By connecting the heater electrode 71 to an external power supply, the heater part 70 can be fed with power from an outside source.

The heater 72 is an electric resistor formed so as to be sandwiched between the second substrate layer 2 and the third substrate layer 3 with respect to a vertical direction. The heater 72 is connected to the heater electrode 71 via the through hole 73, and generates heat when fed with power from an outside source through the heater electrode 71 in order to heat a solid electrolyte forming the sensor element 101 and keep it warm.

The heater 72 is buried across a region extending from the first internal space 20 to the second internal space 40, and can thereby adjust the entire sensor element 101 to a temperature at which the above-mentioned solid electrolyte is activated.

The heater insulating layer 74 is an insulating layer formed of an insulator, such as alumina, on upper and lower surfaces of the heater 72. The heater insulating layer 74 is formed for the purpose of providing electrical insulation between the second substrate layer 2 and the heater 72, and between the third substrate layer 3 and the heater 72.

The pressure diffusion hole 75 is provided so as to penetrate the third substrate layer 3 and communicate with the reference gas introduction space 43, and is formed for the purpose of reducing a rise in internal pressure caused by a temperature rise in the heater insulating layer 74.

<Pump Reference Processing>

Figure 2:
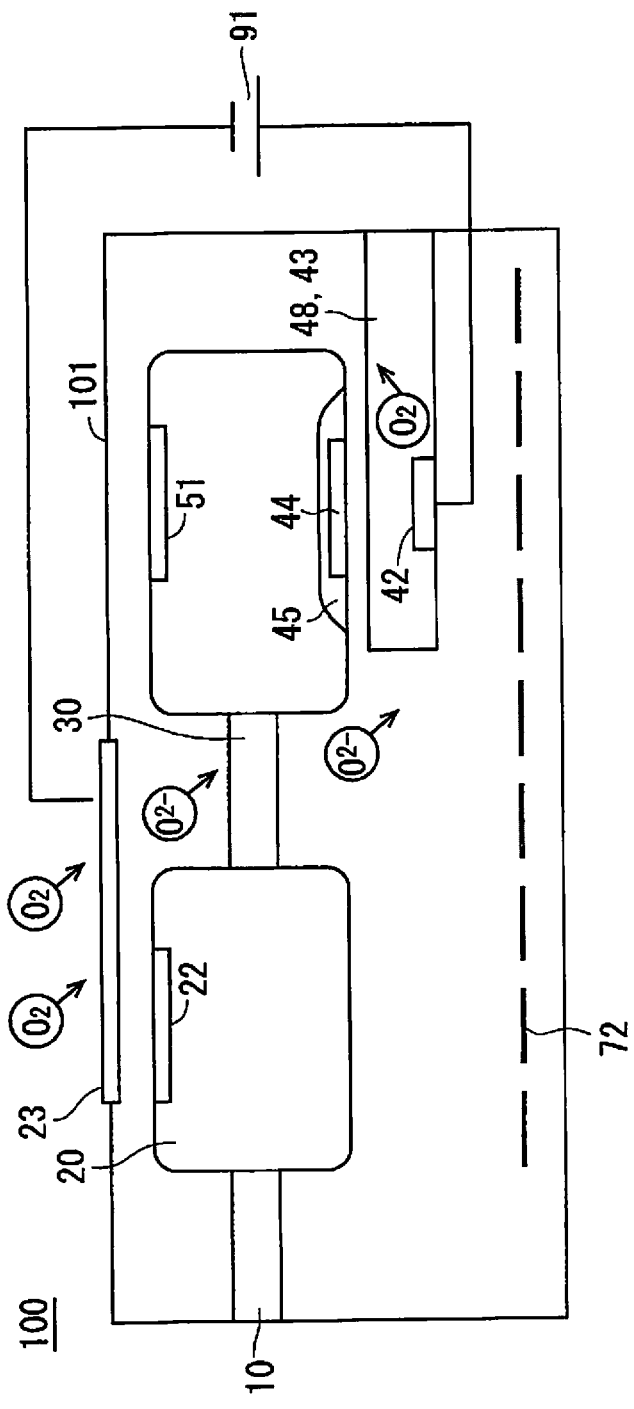
FIG. 2 is a schematic cross section of the gas sensor 100 for describing pump reference processing.

The pump reference processing performed on the gas sensor 100 is outlined next. In the present embodiment, the pump reference processing is performed to stabilize (keep constant) an oxygen concentration in the vicinity of a surface of the reference electrode 42 when the gas sensor 100 is used. In other words, the pump reference processing is processing to stabilize the oxygen concentration in the vicinity of the surface of the reference electrode 42 (oxygen concentration stabilizing processing). FIG. 2 is a schematic cross section of the gas sensor 100 for describing the pump reference processing. In FIG. 2, only some of the components of the gas sensor 100 shown in FIG. 1 are shown, and the other components are simplified or omitted.

In the pump reference processing, as shown in FIG. 2, the reference electrode 42 is electrically connected to a positive terminal of an external DC power supply 91, the outer pump electrode 23 is electrically connected to a negative terminal of the external DC power supply 91, and a DC voltage is applied across the outer pump electrode 23 and the reference electrode 42 to supply oxygen to the vicinity of the surface of the reference electrode 42.

More specifically, when the voltage is applied across the electrodes by the external DC power supply 91, in the outer pump electrode 23, oxygen is ionized upon reception of electrons and taken into the sensor element 101, whereas, in the reference electrode 42, oxygen ions having moved through the sensor element 101, which is formed of an oxygen ion conductive solid electrolyte, are oxidized to oxygen upon release of electrons, and the oxygen remains in the vicinity of the surface of the reference electrode 42.

A timing at which the pump reference processing is performed may be determined appropriately in accordance with a use condition of the gas sensor 100, but, in a case where the gas sensor 100 is mounted on an exhaust pipe of an automobile for use, for example, the pump reference processing is preferably performed at start-up of an engine of the automobile, during idling, or at all times during driving of the sensor.

Excessive pump reference processing is not desirable as it causes an increase in electrical impedance (resistance) between the outer pump electrode 23 and the reference electrode 42, a deviation, from an assumed value, of electromotive force provided between the measurement electrode 44 and the outer pump electrode 23 or at another location during operation of the sensor element, poor responsiveness of the sensor element, and the like. These events are considered to occur as a result of pronounced oxidation of the reference electrode 42 caused due to an excessive increase in oxygen concentration in the vicinity of the surface of the reference electrode 42. The pump reference processing should therefore be performed on condition that oxidation of the reference electrode 42 does not progress.

In the present embodiment, in this regard, a voltage applied by the external DC power supply 91 in the pump reference processing is set to 0.2 V to 4.0 V, and an application time in a single process is set to 2 msec to 1 sec. Since the pump reference processing is performed when the gas sensor 100 is actually used, the temperature of the sensor element 101 (an element temperature) is set approximately to 700° C. to 900° C. due to heating by the heater 72.

<Reverse Voltage Application Processing>

As described above, the pump reference processing for stabilizing the oxygen concentration in the vicinity of the surface of the reference electrode 42 should be performed on condition that oxidation of the reference electrode 42 does not progress. When the gas sensor 100 is actually used, however, the reference electrode 42 may be oxidized after the pump reference processing even if the pump reference processing is performed on the above-mentioned condition, as long as the phenomenon of oxidation includes a time-dependent factor. In addition, the reference electrode 42 may be oxidized in the course of manufacture of the gas sensor 100, although the degree of oxidation may be small. This means that whether the reference electrode 42 is oxidized or not depends not only on how to perform the pump reference processing but also on manufacturing conditions and use conditions of individual gas sensors 100. Therefore, oxidation of the reference electrode 42 is not perfectly prevented even if the applied voltage and the application time in the pump reference processing are set so as to fall within the above-mentioned ranges.

Figure 3:
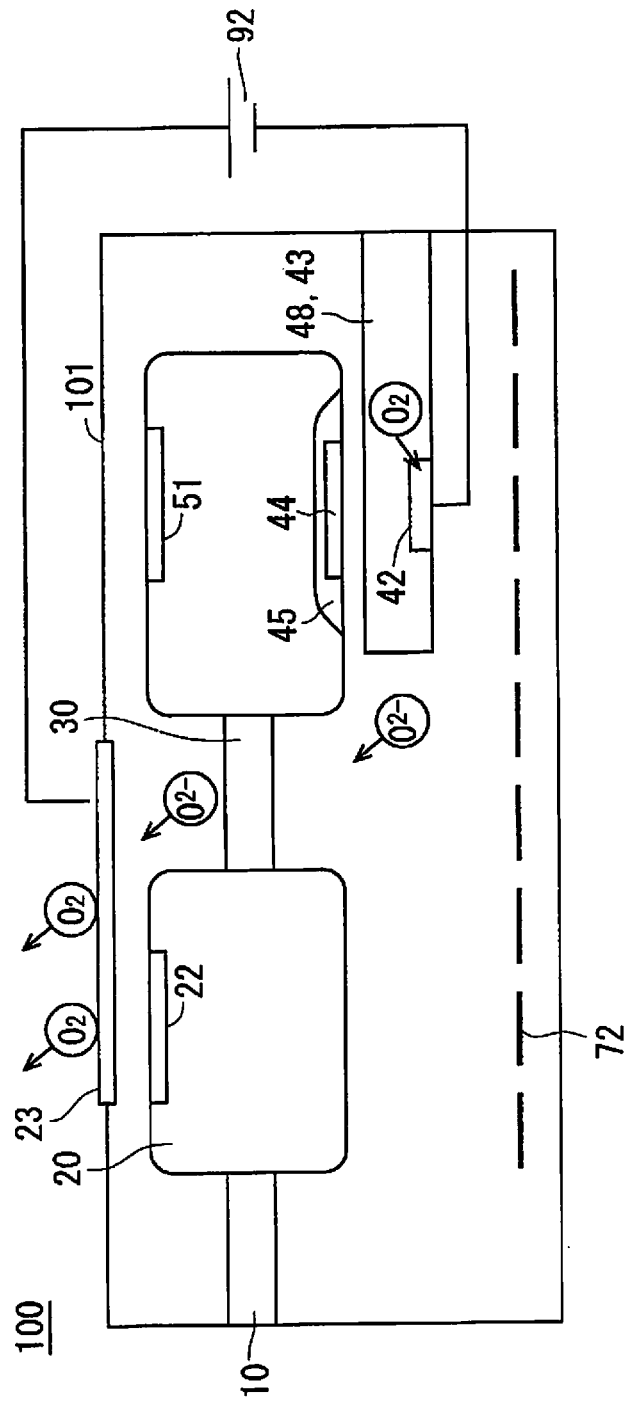
FIG. 3 is a schematic cross section of the gas sensor 100 for describing reverse voltage application processing.

In this regard, in the present embodiment, processing to reliably suppress oxidation of the reference electrode 42 (reverse voltage application processing) is performed. FIG. 3 is a schematic cross section of the gas sensor 100 for describing the reverse voltage application processing. In FIG. 3, only some of the components of the gas sensor 100 shown in FIG. 1 are shown, and the other components are simplified or omitted as in FIG. 2.

In the reverse voltage application processing, as shown in FIG. 3, the reference electrode 42 is electrically connected to a negative terminal of an external DC power supply 92, the outer pump electrode 23 is electrically connected to a positive terminal of the external DC power supply 92, and a DC voltage is applied across the outer pump electrode 23 and the reference electrode 42 to remove oxygen from the vicinity of the surface of the reference electrode 42.

In terms of electrical connection, the reverse voltage application processing is processing performed by reversing a direction of the voltage applied in the pump reference processing. As long as a positive or negative direction of the applied voltage can be reversed appropriately, the external DC power supply 91 and the external DC power supply 92 may be unified.

More specifically, when the voltage is applied across the electrodes by the external DC power supply 92, in the reference electrode 42, oxygen existing in the vicinity of the surface of the reference electrode 42 is ionized upon reception of electrons and taken into the sensor element 101. In a case where oxides (metal oxides) have been formed through oxidation of the reference electrode 42, the oxides are reduced at the same time. That is to say, oxygen atoms are ionized, and the remaining metal atoms (e.g., Pt atoms) become a part of the reference electrode 42 again. It can be said that the reverse voltage application processing is processing to reduce oxides derived from the reference electrode 42 to cause metal atoms to function as the part of the reference electrode 42 again.

In the outer pump electrode 23, oxygen ions having moved through the sensor element 101, which is formed of an oxygen ion conductive solid electrolyte, are oxidized to oxygen upon release of electrons, and the oxygen is discharged to the outside of the sensor element 101.

As for the applied voltage and the application time in the reverse voltage application processing, the effects generally tend to be enhanced as the applied voltage is increased, and as a processing time is increased. The effects of the reverse voltage application processing can be evaluated with use of an impedance value (resistance value) between the outer pump electrode 23 and the reference electrode 42. The impedance value tends to be reduced as the degree of oxidation of the reference electrode 42 decreases. The impedance value can be obtained, for example, from a current value and an applied voltage value obtained when a constant voltage is applied across the outer pump electrode 23 and the reference electrode 42.

An excessively high applied voltage or an excessively long processing time, however, is not desirable, as it causes dissociation of oxygen from an oxygen ion conductive solid electrolyte forming the sensor element 101, which is a phenomenon of so-called element blackening. Even if the element blackening does not occur, it is also not desirable to perform the reverse voltage application processing on a condition that pronouncedly reduces or cancels out the effects of the pump reference processing.

Specifically, it is preferable to at least set a maximum value of the applied voltage to 1.4 V to 2.0 V inclusive, and set the application time to 10 seconds to 1200 seconds inclusive. In this case, the impedance value between the outer pump electrode 23 and the reference electrode 42 can preferably be reduced.

Alternatively, when the maximum value of the applied voltage is set to 2.0 V to 2.1 V inclusive, certain effects can be obtained even if the application time is 10 seconds or less. When the maximum value of the applied voltage is set to 2.1 V, certain effects can be obtained if the application time is 30 seconds or less.

Application of the voltage may continuously or intermittently be repeated, but, in this case, the total voltage application time from the start to the end of a series of repeating processes should not exceed 1200 seconds.

Figure 4:
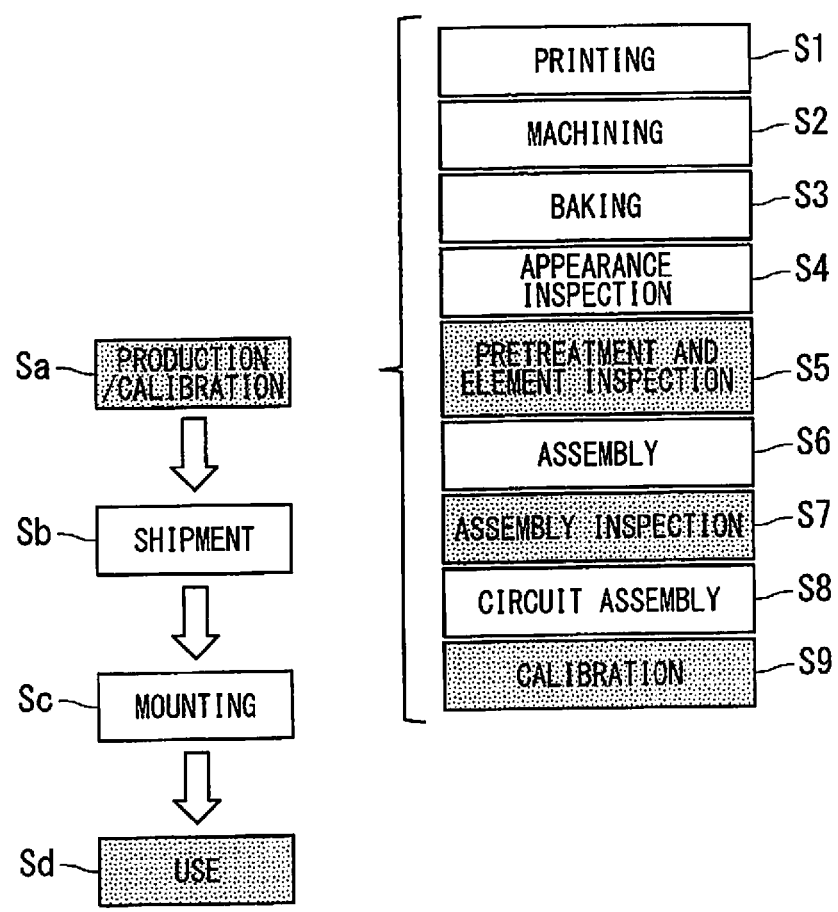
FIG. 4 shows timings at which the reverse voltage application processing is performed in the process from production to use of the gas sensor 100.

A timing at which the reverse voltage application processing is performed is described next. FIG. 4 shows timings at which the reverse voltage application processing is performed in the process from production to use of the gas sensor 100. As shown in FIG. 4, the gas sensor 100 generally undergoes a production/calibration step of bringing the gas sensor 100 to a saleable condition (step Sa), a shipment step of providing or selling the gas sensor 100 to a user (step Sb), and a mounting step, performed by the user, of mounting the gas sensor 100 on a target for concentration measurement (step Sc) before (actual) use (step Sd). From among these steps, steps suitable for performing the reverse voltage application processing are shaded steps in the production/calibration step shown in FIG. 4 and the actual use step.

More specifically, as shown in FIG. 4, the production/calibration step includes the following steps:

a printing step of printing predetermined circuit patterns and the like on ceramic green sheets formed of oxygen ion conductive solid electrolytes (step S1);

a machining step of, after appropriately punching the ceramic green sheets having undergone printing, for example, adhesively laminating the ceramic green sheets, and cutting the resulting laminated body in units of elements (step S2);

a baking step of baking the element body for integration to obtain the sensor element 101 (step S3);

an appearance inspection step of inspecting the appearance of the sensor element 101 obtained through baking (step S4);

a pretreatment and element inspection step of performing predetermined pretreatment on the sensor element 101 having cleared the appearance inspection, and then inspecting electrical characteristics thereof (step S5);

an assembly step of assembling the sensor element 101 having cleared the element inspection to a protective cover and the like to obtain the gas sensor 100 (step S6);

an assembly inspection step of carrying out inspection to check the quality of the assembly of the gas sensor 100 (step S7);

a circuit assembly step of assembling a control circuit to the gas sensor 100 having cleared the assembly inspection (step S8); and a calibration step of calibrating sensitivity characteristics and the like of the gas sensor 100 to which the control circuit has been assembled (step S9).

From among these steps, the reverse voltage application processing can be performed before and after or during the pretreatment and element inspection step, the assembly inspection step, and the calibration step.

As described above, since the primary purpose of the reverse voltage application processing is to suppress progress of oxidation of the reference electrode 42 and to reduce oxides derived from the reference electrode 42, processing conditions are ideally set so as not to excessively reduce oxygen existing in the vicinity of the reference electrode 42 while reducing all the oxides of the reference electrode 42 existing at the start of the processing.

When the gas sensor 100 is actually used, however, it is difficult to spend a long time to perform the reverse voltage application processing and a timing at which the reverse voltage application processing is performed is limited, as measurement of a NOx concentration, which is processing to be originally performed, cannot be performed during the reverse voltage application processing. Before the gas sensor 100 is actually used, i.e., during manufacture of the gas sensor 100, it is relatively easier to secure a time to perform the reverse voltage application processing without hurting productivity, compared to when the gas sensor 100 is actually used.

Therefore, it is preferable to set application times and processing conditions of different ranges in the reverse voltage application processing between the production/calibration step and the actual use step, from among the steps shown in FIG. 4. Specifically, if the reverse voltage application processing is performed in the production/calibration step, it is preferable to set a long processing time to sufficiently reduce an impedance value between the outer pump electrode 23 and the reference electrode 42, and, if the reverse voltage application processing is performed when the gas sensor 100 is actually used, it is preferable to set a short processing time. In the latter case, the degree to which the impedance value is reduced by a single reverse voltage application process is small, but the progress of oxidation of the reference electrode 42 can preferably be suppressed by performing the reverse voltage application processing itself at a certain frequency or higher.

In a case where the gas sensor 100 is mounted on an exhaust pipe of an automobile for use, it is preferable to perform the reverse voltage application processing each time after stopping driving or under a lean atmosphere (air ratio $\lambda>1$), for example, during fuel cut.

Figure 5A:
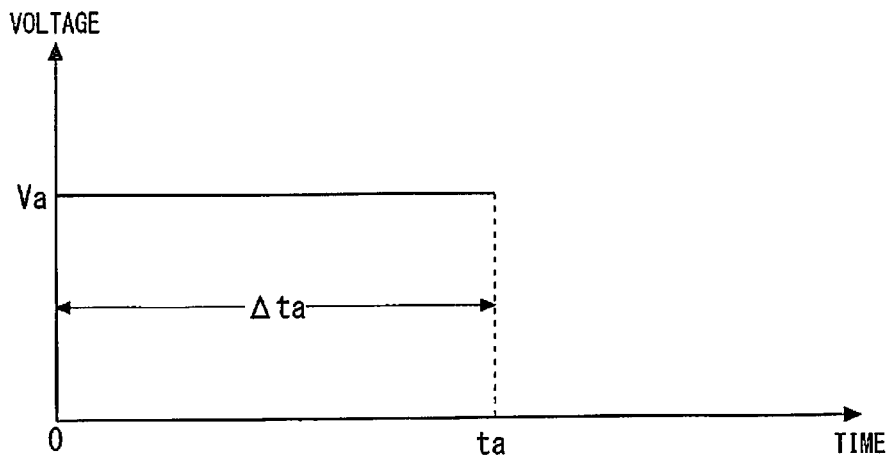
FIGS. 5A, 5B, and 5C show examples of a functional relationship between an applied voltage and an application time suitable for the reverse voltage application processing.
Figure 5B:
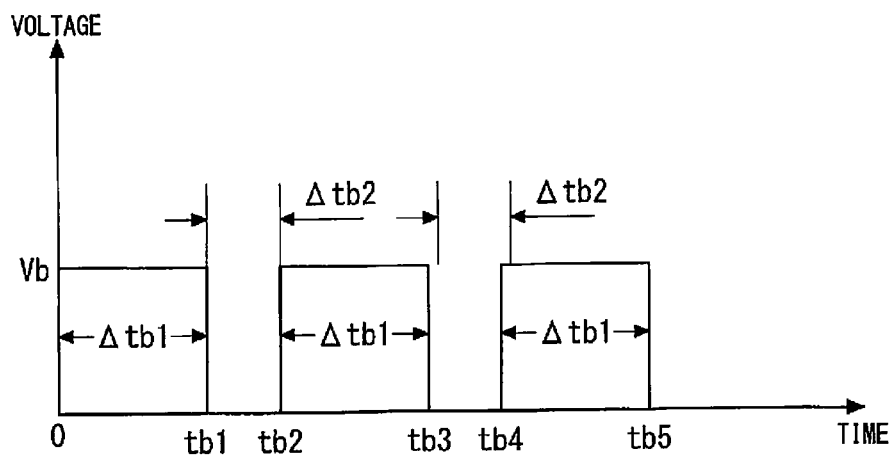
Figure 5C:
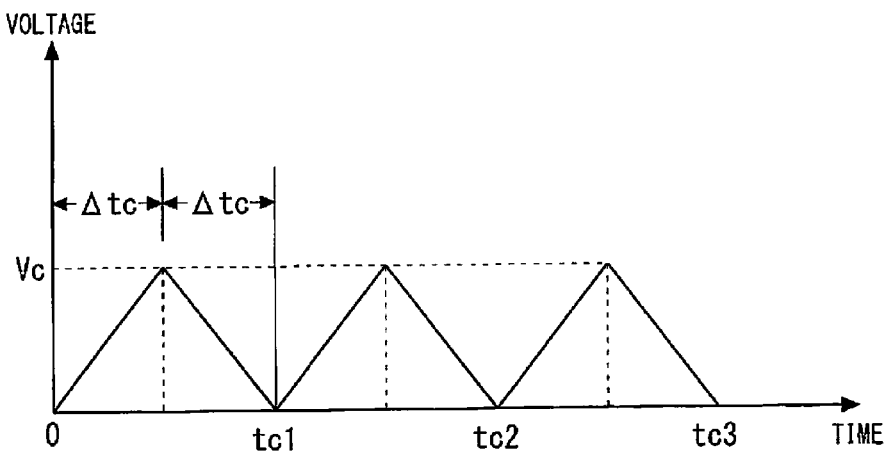

How to provide the applied voltage (the functional relationship between the applied voltage and the application time) in a single reverse voltage application process may be set variously. FIGS. 5A, 5B, and 5C show examples of the functional relationship between the applied voltage and the application time suitable for the reverse voltage application processing.

For example, FIG. 5A shows a case where a pulse-like voltage is applied. Specifically, in the case of FIG. 5A, a constant voltage Va is applied for a predetermined time period $\Delta ta$ from time $t=0$ to time $t=ta$.

FIG. 5B shows a case where application of a voltage for a predetermined time period and suspension of the application are repeated. Specifically, in the case of FIG. 5B, after a constant voltage Vb is applied for a predetermined time period Δtb1 from time t=0 to time t=tb1, the application of the voltage is suspended for a predetermined time period Δtb2 until time t=tb2, and, after the voltage Vb is applied for the time period Δtb1 until time t=tb3, the application of the voltage is suspended for the predetermined time period Δtb2 until time t=tb4, and the voltage Vb is finally applied for the time period Δtb1 until time t=tb5.

FIG. 5C shows a case where a triangular wave voltage is applied. Specifically, in the case FIG. 5C, a linear increase in voltage value from 0 to Vc and a linear decrease in voltage value from Vc to 0 are alternated for each predetermined time period Δtc for a time period from time t=0 to time t=tc1, for a time period from time t=tc1 to time t=tc2, and for a time period from time t=tc2 to time t=tc3.

An element temperature when the reverse voltage application processing is performed is preferably set so as to be equal to or lower than the temperature when the gas sensor 100 is actually used (the temperature equivalent to that in the pump reference processing). Specifically, it is desirable that the element temperature be in a range of 700° C. to 850° C. inclusive. In this case, an impedance value between the outer pump electrode 23 and the reference electrode 42 can preferably be reduced. It is more desirable that the element temperature be in a range of 810° C. to 830° C. inclusive. In this case, the impedance value can be reduced more significantly compared to a case where the element temperature is set to other temperatures. The element temperature when the reverse voltage application processing is performed can be achieved through heating by the heater 72.

As described above, according to the present embodiment, the progress of oxidation of the reference electrode can be suppressed by electrically connecting the reference electrode of the gas sensor to the negative terminal of the external DC power supply, electrically connecting the outer pump electrode to the positive terminal of the external DC power supply, and applying the DC voltage of the predetermined value across the outer pump electrode and the reference electrode for the predetermined time period. The condition of the reference electrode is thereby stabilized, and thus reduction in measurement accuracy of the gas sensor can be suppressed.

EXAMPLES

Example 1

A total of 60 gas sensors 100 were prepared through the steps S1 to S9 of FIG. 4, the reverse voltage application processing was performed on the gas sensors 100 on different applied voltage and application time conditions, and the amount of change in impedance value (resistance value) between the outer pump electrodes 23 and the reference electrodes 42 after and before the processing was measured. Specifically, pulse-like voltages as shown in FIG. 5A were applied. The applied voltage (Va) was set to the following 10 different levels: 0.5 V, 1.0 V, 1.4 V, 1.5 V, 1.6 V, 1.7 V, 1.8 V, 2.0 V, 2.1 V, and 2.5 V. The processing time (Δta) was set to the following six different levels: 1 sec, 10 sec, 20 sec, 30 sec, 150 sec, and 1200 sec. The element temperature was set to 850° C.

Table 1 shows measurement results for each condition. In Table 1, a case where the amount of change in impedance value (resistance value) before and after the reverse voltage application processing was particularly large, i.e., 400Ω or more, is represented by a double circle (Class 1), a case where the amount of change was relatively large, i.e., 100Ω or more to less than 400Ω, is represented by a single circle (Class 2), and a case where the amount of change was small, i.e., less than 100Ω, is represented by a triangle (Class 3). A case where element blackening occurred is represented by a cross (Class 4).

TABLE 1

|  |  | APPLICATION TIME (sec) | | | | | |
| --- | --- | --- | --- | --- | --- | --- | --- |
|  |  | 1 | 10 | 20 | 30 | 150 | 1200 |
| APPLIED VOLTAGE (V) | 0.5 | Δ | Δ | Δ | Δ | Δ | Δ |
|  | 1 | Δ | Δ | Δ | Δ | Δ | Δ |
|  | 1.4 | Δ | ○ | ○ | ○ | ○ | ◎ |
|  | 1.5 | Δ | ○ | ○ | ○ | ○ | ◎ |
|  | 1.6 | Δ | ○ | ○ | ○ | ◎ | ◎ |
|  | 1.7 | Δ | ○ | ○ | ○ | ◎ | ◎ |
|  | 1.8 | Δ | ○ | ○ | ○ | ◎ | ◎ |
|  | 2 | ○ | ○ | ○ | ○ | ◎ | ◎ |
|  | 2.1 | ○ | ○ | ○ | ○ | X | X |
|  | 2.5 | X | X | X | X | X | X |

◎: PARTICULARLY LARGE RESISTANCE REDUCING EFFECTS (CLASS 1)
○: LARGE RESISTANCE REDUCING EFFECTS (CLASS 2)
Δ: SMALL RESISTANCE REDUCING EFFECTS (CLASS 3)
X: OCCURRENCE OF ELEMENT BLACKENING (CLASS 4)

As shown in Table 1, at least in a case where the applied voltage was set to 1.4 V to 2.0 V inclusive and the application time was set to 10 seconds to 1200 seconds inclusive, the measurement results were categorized as Class 1 or Class 2. This indicates that the effects of the reverse voltage application processing can preferably be obtained in these condition ranges.

Particularly, in a case where the applied voltage was set to 1.6 V to 2.0 V inclusive and the application time was set to 150 seconds to 1200 seconds inclusive, and in a case where the applied voltage was set to 1.4 V to 1.6 V inclusive and the application time was set to 1200 seconds, the measurement results were categorized as Class 1. It can be said that these conditions are suitable when the reverse voltage application processing is performed prior to actual use of the gas sensor 100, as in this example.

In a case where the maximum value of the applied voltage was set to 2.0 V to 2.1 V inclusive, the measurement results were categorized as Class 2 even if the application time was equal to or shorter than 10 seconds. In a case where the maximum value of the applied voltage was set to 2.1 V, the measurement results were categorized as Class 2 if the application time was equal to or shorter than 30 seconds.

Conditions on which the measurement results were categorized as Class 2 are considered to be suitable for performing the reverse voltage application processing when the gas sensor 100 is actually used.

Example 2

A total of five gas sensors 100 were prepared through the steps S1 to S9 of FIG. 4, the reverse voltage application processing was performed on the gas sensors 100 on different element temperature conditions, and the amount of change in impedance value (resistance value) between the outer pump electrodes 23 and the reference electrodes 42 after and before the processing was measured. The element temperature was set to the following five different levels: 650° C., 700° C., 820° C., 850° C., and 900° C. Pulse-like voltages as shown in FIG. 5A were applied, the applied voltage was set to 1.6 V, and the processing time was set to 30 sec.

Table 2 shows measurement results for each condition. In Table 2, the degree of change in impedance value is shown based on similar criteria to those in Table 1.

TABLE 2

| ELEMENT TEMPERATURE (° C.) | | | | |
|---|---|---|---|---|
| 650 | 700 | 820 | 850 | 900 |
| Δ | ◯ | ⊚ | ◯ | Δ |

⊚: PARTICULARLY LARGE RESISTANCE REDUCING EFFECTS
◯: LARGE RESISTANCE REDUCING EFFECTS
Δ: SMALL RESISTANCE REDUCING EFFECTS

As shown in Table 2, impedance value (resistance value) reducing effects could be obtained when the element temperature was in a range of 700° C. to 850° C., and, in particular, the most notable effects could be obtained when the element temperature was 820° C.

While the invention has been shown and described in detail, the foregoing description is in all aspects illustrative and not restrictive. It is therefore understood that numerous modifications and variations can be devised without departing from the scope of the invention.

What is claimed is:

1. A method for performing processing on a gas sensor having a sensor element containing an oxygen ion conductive solid electrolyte as a major component, said sensor element including:
an internal space into which a measurement gas is introduced from an external space;
a first electrode formed on a surface of said internal space;
a second electrode formed on an external surface of said sensor element; and
a reference electrode provided inside said sensor element, said sensor element being configured to be capable of pumping out oxygen in said internal space by applying, across said first electrode and said second electrode, a predetermined voltage determined based on a potential difference between said first electrode and said reference electrode, said sensor element being configured to be capable of stabilizing an oxygen concentration in the vicinity of a surface of said reference electrode by electrically connecting said reference electrode to a positive terminal of a first external DC power supply, electrically connecting said second electrode to a negative terminal of said first external DC power supply, and continuously or intermittently applying a DC voltage across said reference electrode and said second electrode, said method comprising the steps of:
a) electrically connecting said reference electrode to a negative terminal of a second external DC power supply, and electrically connecting said second electrode to a positive terminal of said second external DC power supply; and
b) in an electrically-connected state created by said step a), applying a DC voltage having a maximum value of 1.4 V to 2.0 V inclusive across said reference electrode and said second electrode for 10 seconds to 1200 seconds inclusive while setting temperature of said sensor element to 700° C. to 850° C. inclusive.

2. The method for performing processing on the gas sensor according to claim 1, wherein
said step b) is performed during manufacture of said gas sensor.

3. The method for performing processing on the gas sensor according to claim 1, wherein
said step b) is performed when said gas sensor is used.

4. A method for performing processing on a sensor element for use in a gas sensor, the sensor element containing an oxygen ion conductive solid electrolyte as a major component, said sensor element having:
an internal space into which a measurement gas is introduced from an external space;
a first electrode formed on a surface of said internal space;
a second electrode formed on an external surface of said sensor element; and
a reference electrode provided inside said sensor element, said sensor element being configured to be capable of pumping out oxygen in said internal space by applying, across said first electrode and said second electrode, a predetermined voltage determined based on a potential difference between said first electrode and said reference electrode, said sensor element being configured to be capable of stabilizing an oxygen concentration in the vicinity of a surface of said reference electrode by electrically connecting said reference electrode to a positive terminal of a first external DC power supply, electrically connecting said second electrode to a negative terminal of said first external DC power supply, and continuously or intermittently applying a DC voltage across said reference electrode and said second electrode, said method comprising the steps of:
a) electrically connecting said reference electrode to a negative terminal of a second external DC power supply, and electrically connecting said second electrode to a positive terminal of said second external DC power supply; and
b) in an electrically-connected state created by said step a), applying a DC voltage having a maximum value of 1.4 V to 2.0 V inclusive across said reference electrode and said second electrode for 10 seconds to 1200 seconds inclusive while setting temperature of said sensor element to 700° C. to 850° C. inclusive.

* * * * *